United States Patent
Kobayashi

(10) Patent No.: US 6,838,527 B2
(45) Date of Patent: Jan. 4, 2005

(54) POLYMER-IMMOBILIZED α-IMINOESTER

(75) Inventor: Shu Kobayashi, Tokyo (JP)

(73) Assignee: Japan Science and Technology Corporation, Saitama (JP)

( * ) Notice: Subject to any disclaimer, the term of this patent is extended or adjusted under 35 U.S.C. 154(b) by 0 days.

(21) Appl. No.: 10/221,372

(22) PCT Filed: Mar. 13, 2001

(86) PCT No.: PCT/JP01/01971

§ 371 (c)(1), (2), (4) Date: Nov. 7, 2002

(87) PCT Pub. No.: WO01/68588

PCT Pub. Date: Sep. 20, 2001

(65) Prior Publication Data

US 2003/0187147 A1 Oct. 2, 2003

(30) Foreign Application Priority Data

Mar. 13, 2000 (JP) ........................................ 2000-069499

(51) Int. Cl.$^7$ ...................... C08F 212/08; C07C 227/14; C07C 229/00; C07D 215/36
(52) U.S. Cl. ...................... 525/333.3; 546/155; 560/38; 560/155
(58) Field of Search ........................... 525/333.3, 333.6; 546/155; 560/38, 155, 168; 562/560, 804

(56) References Cited

PUBLICATIONS

T.W. Graham Solomons, Organic Chem. ,second ed. John Wiley & Sons, Inc. 1980. p. 482–500.*
Miyabe, H. et al., J. Org. Chem., vol. 64, No. 7, pp. 2174–2175 (1999).
Kenkyukai ed. "Combinatorial Chemistry; Nyumon kara Ouyou made" Kyoto: Kabushiki Kaisha Kagaku Doujin, pp. 36–38 (1997).

* cited by examiner

*Primary Examiner*—Ceala Tsay
*Assistant Examiner*—Taylor V. Oh
(74) *Attorney, Agent, or Firm*—Wenderoth, Lind & Ponack, L.L.P.

(57) ABSTRACT

As an α-iminoester derivative that is stable under normal conditions and a method of producing various α-aminoester derivatives using them, a polymer-immobilized α-iminoester derivative represented by the following general formula (1):

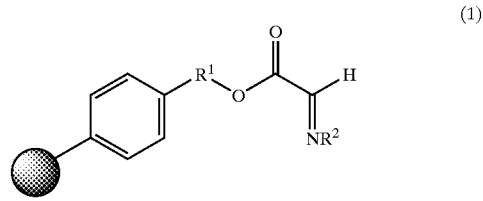

wherein $R^1$ represents an alkyl chain of 1 or more carbons, and $R^2$ represents a hydrogen atom, halogen atom, or an alkyl group, aryl group or alkoxy group that may contain substituents, and a method of producing an α-iminoester derivative using them are provided.

5 Claims, No Drawings

POLYMER-IMMOBILIZED α-IMINOESTER

TECHNICAL FIELD

The invention of the present application relates to a polymer-immobilized α-iminoester. More specifically, the invention of the present application relates to a method of producing an α-aminoester derivative by using a polymer-immobilized α-iminoester.

BACKGROUND ART

The total synthesis of natural materials has become an important subject in various fields such as medicine, agricultural chemicals and perfumes. α-iminoesters are extremely useful as precursors of nitrogen-containing natural compounds such as α-amino acids (*J. Am. Chem. Soc.*, 1989, 111, 2582–2855; *J. Org. Chem.*, 1988, 53, 1298–1307; *J. Org. Chem.*, 1991, 56, 1894–1901) and β-amino alcohols (*J. Org. Chem.*, 1976, 41, 3121–3124; *J. Am. Chem. Soc.*, 1997, 119, 7871–7872), and have attracted much attention. However, the monomer tends to decompose or polymerize at room temperature and is extremely unstable and difficult to handle. For these reasons, α-amino acids had to be prepared just before use, making further progress in their use and development difficult.

The present inventors have previously reported the immobilization of unstable silyl enole ethers on resins and their use in various carbon-carbon bond forming reactions (*Tetrahedron Lett.*, 1996, 37, 2809–2812; *Tetrahedron Lett.*, 1996, 37, 5569–5572; *Tetrahedron Lett.*, 1996, 37, 7783–7736; *Tetrahedron Lett.*, 1997, 38, 4251–4254; *Molecules Online*, 1998, 2, 35–39; *J. Org. Chem.* 1998, 63, 4868–4869). If an α-iminoester could be immobilized on a polymer in the same manner, the compound maybe stabilized and its handling and storage may be made easier. However, because α-iminoesters are unstable on their own, as described above, it was difficult to even introduce them to a polymer.

The invention of the present application has been accomplished in view of the aforementioned situations and its object is to provide α-iminoester derivatives that are stable under ordinary conditions and provide a method of synthesizing various α-aminoester derivatives at high yield using them, thereby overcoming the limitations of the prior art.

DISCLOSURE OF THE INVENTION

In order to accomplish the above-described objects, the invention of the present application firstly provides a polymer-immobilized α-iminoester represented by the following general formula (1):

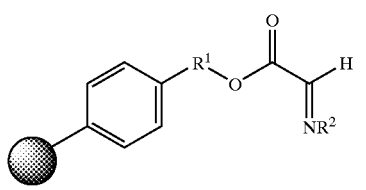

(1)

(wherein $R^1$ represents an alkyl chain of more than 1 carbon atom(s), and $R^2$ represents a hydrogen atom, halogen atom, or an alkyl group, aryl group or alkoxy group that may contain substituents.)

Further, the invention of the present application secondly provides a method of manufacturing an α-aminoester derivative, comprising the use of the above-described polymer-immobilized α-iminoester.

BEST MODE FOR CARRYING OUT THE INVENTION

As described above, the invention of the present application comprises the immobilization of an unstable α-iminoester on to a polymer, and hereinafter, the best mode for practicing the invention is described in detail.

The polymer-immobilized α-iminoester represented by the general formula (1) may be obtained by, for example, the hydrolysis of commercially available ethyldiethoxy acetate, followed by reaction with a chloromethylated resin and treatment of the resulting diethoxy acetate resin with a hydrochloric acid/dioxane solution, after which the active intermediate is reacted with an amine.

In this process, $R^1$ of general formula (1) is an alkyl chain of 1 or more carbon atoms. The length of the alkyl chain may vary depending on the alkyl chain bonded to the phenyl group at the terminus of the resin (although said alkyl chain may also be omitted). Further, a hydrogen atom may be attached to the resin terminus instead of an alkyl chain, in which case, $R^1$ becomes $CH_2$ by the chloromethylation of the resin terminus. Preferably, $R^1$ is an alkyl chain of 1 to 3 carbon atoms.

Further, in the above-described case, $R^2$ differs depending on the amine that is to be reacted; for example, an alkyl group such as methyl, ethyl, n-propyl, i-propyl, n-butyl, sec-butyl, hexyl, cyclohexyl, cyclobutyl or cyclopentyl, an alkylene group such as ethylene, propylene, butylene or amylene, or an aryl group such as phenyl, toluyl or xylyl may be applied. Further, these substituents may further contain substituents. For example, halogenated phenyl group, benzyl group, o-methylphenyl group or p-methoxyphenyl group maybe considered. Preferable examples are p-methoxyphenyl, p-halogenated pheny; of course, $R^2$ is not restricted to these and may be selected according to the desired α-aminoester derivative.

In the invention of the present application, α-amino acids can be obtained at high stereoselectivity and yield, by using the novel polymer-immobilized α-iminoester of the present invention as a starting material and reacting it with a nucleophile. Further, tetrahydroquinoline derivatives can be obtained at a high yield by reacting the above novel substance with various alkenes. Moreover, solid phase aza Diels-Alder reaction can be performed smoothly using the polymer-immobilized α-iminoester of the present invention.

The structure of the nucleophile and the reactants such as alkenes are not particularly limited, and may be selected according to the desired α-aminoester derivative species. Further, reaction conditions such as solvent, temperature and time, are not restricted either.

The invention of the present application is described more specifically by the following Examples. It should be noted that the present invention is not restricted to these Examples.

EXAMPLE

Reference Example 1

Synthesis of Polymer-Immobilized α-Iminoester

A diacetoxy acetate resin was synthesized according to chemical formula [A]. All products obtained after each step of the solid phase reaction were monitored by Swollen-Resin Magic Angle Spinning NMR (SR-MAS NMR).

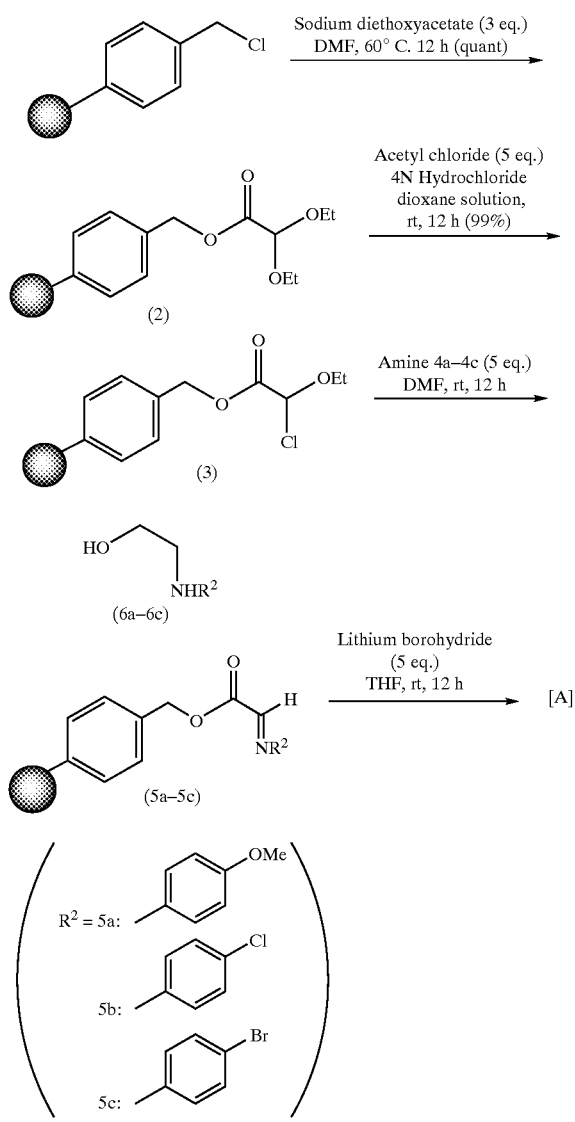

(1) Synthesis of Diethoxyacetate Resin (Compound 2)

To a suspension of chloromethyl copoly-(styrene-1%-divinyl benzene) resin (1.24 mmol/g, 10.0 g, 12.4 mmol) in DMF (100 ml), was added sodium diethoxyacetate (3.0 eq., 6.37 g, 37.2 mmol) and tetra-n-butyl ammonium iodide (1.0 eq., 4.58 g, 12.4 mmol), and stirred under inert atmosphere for 12 hours at 60° C. After the reaction solution was filtered and washed with water, THF and dichloromethane, a diethoxyacetate resin (Compound 2, 1.09 mmol/g) was obtained. The loading of Compound (2) was determined by chlorine titration (Volhard's method). The result of identification was as shown in Table 1.

TABLE 1

Compound (2)

$^{13}C$ SR-MAS NMR (CDCl$_3$) δ = 15.0, 40.3, 62.3, 66.7, 97.3, 125.6, 127.9, 145.3, 167.4
IR (KBr) 1755 cm$^{-1}$ (2) Synthesis of 2-Chloro-2-Ethoxyacetate Resin (Compound 3)

To a suspension of compound (2) (1.09 mmol/g, 10.0 g, 10.9 mmol) in 4N hydrogenchloride dioxane solution (100 ml) was added acetyl chloride (5.0 eq., 3.9 ml, 54.5 mmol) and stirred at room temperature for 12 hours. After the reaction solution was filtered and washed with THF and dichloromethane, a 2-chloro-2-ethoxyacetate resin (Compound 3, yield 99%, 1.10 mmol/g) was obtained. The loading of Compound (2) was determined by chlorine titration (Volhard's method). The result of identification is shown in Table 2.

TABLE 2

Compound (3)

NMR (CDCl$_3$) δ = 14.2, 40.3, 66.3, 67.7, 88.4, 125.6, 127.9, 145.3, 161.1
IR (KBr) 1760 cm$^{-1}$ (3) Synthesis of 2-(4'-Methoxyphenyl)Iminoacetate Resin (Compound 5)

To a suspension of compound (3) (1.10 mmol/g, 181.8 mg, 0.2 mmol) in DMF (100 ml) was added p-anisidine (Compound 4a) (5.0 eq., 123.2 mg, 1.0 mmol) and stirred at room temperature for 12 hours. After the reaction solution was filtered and washed with THF and dichloromethane, a 2-(4'-methoxyphenyl) iminoacetate resin (Compound 5a, 1.10 mmol/g) was obtained. The result of identification was as shown in Table 3.

TABLE 3

Compound (5a)

NMR (CDCl$_3$) δ = 40.3, 55.4, 67.2, 114.5, 123.6, 125.6. 127.9, 141.3, 147.5 160.5, 163.2
IR (KBr) 1760 cm$^{-1}$ (4) Conversion to 2-(4'-methoxyphenyl)Aminoethanol (Compound 6a)

In order to determine the loading of the above-described Compound (5a), 2-(4'-methoxyphenyl)iminoacetate resin was transformed in to 2-(4'-methoxyphenyl) aminoethanol (Compound 6a) by the following procedure.

Compound (5a) and lithium borane (5.0 eq., 21.8 mg, 1.0 mmol) were added to THF (5 ml) and stirred at room temperature for 12 hours. An aqueous 1N HCl solution was added to the reaction solution to terminate reaction, after which saturated sodium hydrogen carbonate was added. The aqueous layer was extracted with dichloromethane and the organic layer was dried over sodium sulfate. After removing the solvent, the crude product was purified by TLC to obtain 2-(4'-methoxyphenyl)aminoethanol (Compound 6a, 33.4 mg). The result of identification is shown below.

TABLE 4

Compound (6a)

$^1$HNMR(CDCl$_3$) δ = 2.71(brs.2H), 3.25(t, 2H,J = 5.2Hz), 3.75(s, 3H), 3.81(t, 2H, J = 5.2Hz), 6.63(d, 2H, J = 9.0Hz), 6.79(d, 2H, J = 9.0Hz):
$^{13}$CNMR(CDCl$_3$) δ=4 7.2, 55.8, 61.3, 114.5, 114.9, 142.2, 152.5:
MS(EI)m/z = 167
IR(KBr)1760cm$^{-1}$ Accordingly, identification results for 2-(4'-chlorophenyl) aminoethanol (6b) obtained by the above steps (3)–(4) using Compound 4b as the amine, and 2-(4'-bromophenyl) aminoethanol (6c) obtained by the above steps (3)–(4) using 4c as the amine, are shown in Table 5 and Table 6, respectively.

TABLE 5

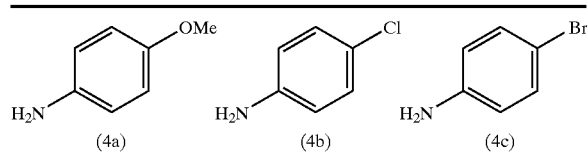

| (4a) | (4b) | (4c) |

Compound (6b)

¹H NMR (CDCl₃) δ = 2.69 (brs. 2H), 3.19 (t, 2H. J = 5.1 Hz), 3.75 (t, 2H, J = 5.2 Hz), 6.50 (d, 2H, J = 8.9 Hz), 7.05 (d, 2H, J = 8.9 Hz):
¹³C NMR (CDCl₃) δ = 46.2. 61.1. 114.9, 122.5, 129.1, 146.6:
MS (EI) m/z = 171

TABLE 6

Compound (6c)

¹HNMR(CDCl₃) δ = 2.73(brs.2H), 3.20(t, 2H.J = 5.1Hz), 3.76(t, 2H, J = 5.1Hz), 6.47(d, 2H, J = 8.8Hz), 7.19(d, 2H, J = 8.9Hz):
¹³CNMR(CDCl₃) δ =46.1, 61.1, 109.6, 114.8, 132.0, 146.9:
MS(EI)m/z = 215

Example 1

Mannich-Type Reaction Using Polymer-Immobilized α-Iminoester

A γ-oxo-α-amino acid derivative was synthesized by the Mannich-type reaction using the polymer-immobilized α-iminoester of the present invention as the starting material in accordance with chemical formula [B]

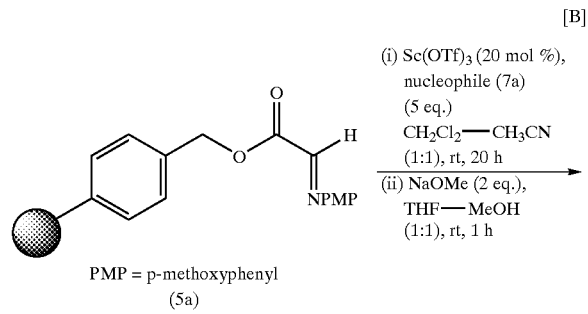

To a suspension of Sc(OTf)₃ (20 mol %, 19.7 mg, 0.04 mmol) and the Compound (5a) (1.10 mmol/g, 181.8 mg. 0.2 mmol) in dichloromethane-acetonitrile (1:1, 3 ml), 1-methoxy-2-methyl-1-trimethylsiloxy-1-propene (Compound 7a, 5.0 eq., 174.3 mg, 1.0 mmol) in dichloromethane-acetonitrile (1:1, 1 ml) was added, and the mixture was stirred at room temperature for 20 hours.

After saturated aqueous sodium hydrogen carbonate was added to quench the reaction, the polymer was filtered and washed with water, THF and dichloromethane, and dried.

The resultant polymer was combined with sodium methoxide (2.0 eq., 1M) in THF-methanol (1:1, 4 ml) and stirred for 1 hour at room temperature. After adding 4N HCl dioxane solution (0.1 ml), the reaction solution was filtered and the solvents were removed from the filtrate under a reduced pressure. The crude product was purified by preparative TLC to afford dimethyl 3,3-dimethyl-2-(4'-methoxyphenyl)aminosuccinate (8a, 44.9 mg, yield 76%).

The identification result is shown below.

TABLE 7

Compound (8a)

¹HNMR(CDCl₃) δ = 1.24(s, 3H), 1.28(s, 3H), 3.65(s, 3H), 3.69(s, 3H), 3.71(s, 3H), 4.23(s, 1H), 6.67(d, 1H, J = 8.8Hz), 6.74(d, 2H, J = 8.8Hz):
¹³CNMR(CDCl₃) δ = 21.6, 22.5, 46.1, 52.0, 52.2, 55.7, 64.9, 114.8, 116.1, 141.2, 153.2, 172.7, 176.1:
IR(neat)1512, 1737, 3378cm⁻¹
MS(EI)m/z = 295

Further, identification results for the products (Compound 8b–8c) obtained by the Mannich reaction of Compound (5a) with various nucleophiles (Compounds 7b–7e) other than 1-methyxo-2-methyl-1-polymethyl siloxy-1-propene (Compound 7a) shown in Table 8 are indicated in Tables 8 to 12. Particularly, when Danishefsky's diene (*J. Am. Chem. Soc.*, 1974, 96, 7807–7809; *Tetrahedron Lett.*, 1982, 23, 3739–3742) was used as a nucleophile, 2-methoxycarbonyl-1-(4'-methoxyphenyl)-1,2,3,4-tetrahydropyridin-2-on (Compound 8e) was obtained in 69% yield.

TABLE 8

(8a–d)

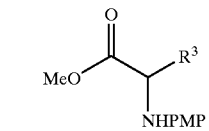

| Nucleophile | Product | Yield (%)ᵃ |
|---|---|---|
| (7a) 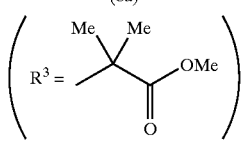 OSiMe₃ OMe | (8a) R³ = Me Me OMe O | 76 |
| (7b) OBn OSiMe₃ (Z) OPh | (8b) R³ = OBn OMe O | 94ᵇ |

TABLE 8-continued (8a–d)

MeO—C(=O)—CH(R³)—NHPMP

| Nucleophile | Product | Yield (%)[a] |
|---|---|---|
| (7c) OSiMe₃ / Ph | (8c) R³ = CH₂—C(=O)—Ph | 71[c] |
| (7d) OSiMe₃ / Ph (Me) | (8d) R³ = CH(Me)—C(=O)—Ph | 65[c,d] |
| (7e) OSiMe₃ / OMe (E) | (8d) MeO₂C—[ring: N(PMP), C=O, Z] | 69[3] |

[a]Based on (5a),
[b]Diastereomer ratio = 60:40,
[c]Sc(OTf)3 (40 mol %) used,
[d]Diastereomer ratio not determined,
[e]Reaction at −5° C.

TABLE 9

Compound (8b)

(major):¹HNMR(CDCl₃) δ = 3.50(s, 3H), 3.64(s, 3.H), 3.68(s, 3H), 4.37(d, 1H, J= 11.9Hz), 4.41–4.53(m.2H), 4.61 (s, 1H), 4.83(d, 1H, J = 11.9Hz), 6.54(d, 2H, J = 8.8Hz), 6.66 (d, 2H, J = 8.8Hz), 7.16–7.35(m, 5H):¹³CNMR(CDCl₃)
δ = 52.3, 52.4, 53.6, 60.8, 65.3, 73.0, 114.6,
116.1, 128.1, 128.2, 128.4, 136.7, 140.6, 153.2, 170.2, 171.1:(minor):
¹HNMR(CDCl₃) δ = 3.658(s, 3H), 3.661(s, 3H), 3.73(s, 3H), 4.27(d, 1H, J = 3.7 Hz), 4.37(d, 1H,J = 11.7Hz), 4.47)(d, 1H, J = 3.7Hz), 4.62(s, 1H), 4.76(d, 1H, J = 11.7Hz), 6.52(d, 2H, J = 8.8Hz), 6.68(d, 2H, J = 8.8Hz), 7.20–7.35(m, 5H):¹³C NMR(CDCl₃) δ = 52.3, 52.5, 55.6, 60.3, 73.2, 77.7, 114.9, 115.7, 127.9, 128.0, 128.4, 136.8, 139.4, 153.1, 170.3, 170.5:IR(neat)1514, 1752, 3371cm⁻¹:MS(EI)m/z = 373.

TABLE 10

Compound (8c)

¹HNMR(CDCl₃) δ = 3.47(d, 2H, J = 3.4Hz), 3.65(s, 3H), 3.66(s, 3H),
4.48(t, 1H, J = 5.4Hz).
6.60(d, 2H, J = 8.9Hz), 6.70(d, 2H, J = 8.9Hz). 7.35 –7.55(m, 3H), 7.80–7.90(m, 2H):
¹³CNMR(CDCl₃) δ = 41.1, 52.4, 54.2, 55.6, 114.8, 115.6, 128.1, 128.7, 133.5, 136.3, 140.4, 153.0, 173.7, 197.3:IR(neat)1513, 1632, 1729, 3365cm⁻¹:MS(EI)m/z = 313.

TABLE 11

Compound (8d)

¹HNMR(CDCl₃) δ= 1.22–1.36(m, 3H), 3.58–3.65(m, 3H), 3.67–3.74(m, 3H), 3.92–4.06 (m, 1H), 4.32–4.41(m, 1H), 6.49–6.77(m, 4H), 7.36–7.61 (m, 3H), 7.87(d, 2H, J=7.3 Hz):¹³CNMR(CDCl₁) δ = 13.6, 14.8, 43.2, 43.8, 52.0, 52.2, 55.6, 60.2, 61.0, 114.7, 115.6, 115.8, 128.28, 128.30, 128.70, 128.73, 133.21, 133.29, 135.9, 136.4, 140.6, 140.9, 152.9, 153.0, 173.4, 173.3, 201.3, 201.8:IR(neat)1514, 1682, 1736, 3389cm⁻¹: MS(EI)m/z = 261.

TABLE 12

Compound (8e)

$^1$HNMR(CDCl$_3$) δ = 2.90(dq, 1H, J=1.1, 16.8Hz), 3.05(dd, 1H, J = 7.5, 16.8 Hz), 3.739(s, 3H), 3.78(s, 3H), 4.67(dd, 1H, J = 1.1, 7.5Hz), 5.18(d, 1H, J = 7.7Hz), 6.88(d, 2H, J = 9.0Hz), 7.06(d, 2H, J = 9.0Hz), 7.38(dd, 1H, J = 1.1, 7.7Hz):$^{13}$C NMR(CDCl$_3$) δ = 38.3, 53.0, 55.5, 61.1, 101.8, 114.7, 121.8, 138.1, 150.0, 157.3, 170.3, 189.0:IR(neat)1509, 1581, 1652, 1743cm$^{-1}$:MS(EI)m/z = 327.

Example 2

Synthesis of Tetrahydroquinoline Derivatives Using Polymer-Immobilized α-Iminoester Tetrahydroquinoline derivatives were synthesized according to the reaction of chemical formula [C].

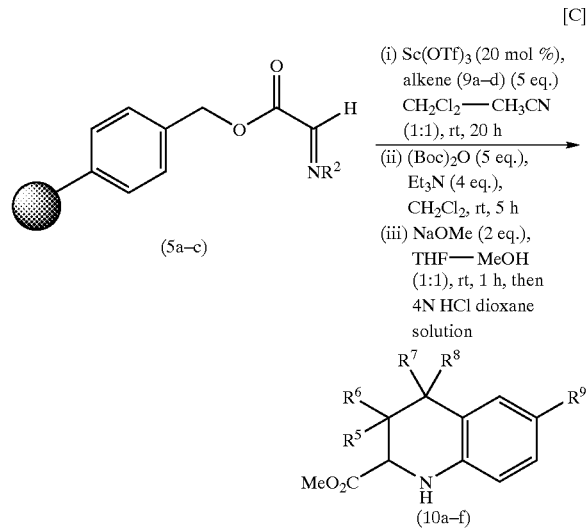

To a suspension of Sc(OTf)$_3$ (20 mol %, 19.7 mg, 0.04 mmol) and Compound (5a) (1.10 mmol/g, 181.8 mg, 0.2 mmol) in dichloromethane-acetonitrile (1:1, 3 ml), a solution of 2,3-dihydropropane (Compound 9a, 5.0 eq., 70.1 mg, 1.0 mg, 1.0 mmol) in dichloromethane-acetonitrile (1:1, 1 ml) was added and stirred at room temperature for 20 hours.

(9a)

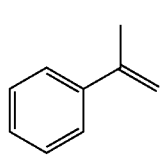
(9b)

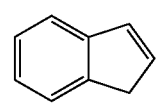
(9c)

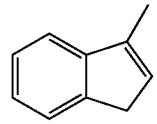
(9d)

After the addition of saturated aqueous sodium hydrogen carbonate to quench the reaction, the resin was filtered and washed with water, THF and dichloromethane, and dried.

The resulting polymer and sodium methoxide (2.0 eq., 1M) were added to THF-methanol (1:1, 4 ml) and stirred at room temperature for one hour. After adding 4N HCl dioxane solution (0.1 ml), the reaction solution was filtered and the solvent was removed under a reduced pressure. The crude product was purified by preparative TLC to obtain 8-methoxy-4-methoxycarbonyl-2,3,3a,4,5,9b-hexahydrofurano [C]-quinoline (Compound 10a, 37.9 mg, yield 72%).

The identification result is shown in Table 13.

TABLE 13

Compound (10a)

| | |
|---|---|
| $^1$HNMR(CDCl$_3$)δ = | 1.82–1.92(m, 1H), 1.95–2.06(m, 1H), 3.07(dq, 1H, J=3.2, 8.6Hz), 3.65–3.90(m, 7H), 4.44(d, 1H, J=3.2Hz), 5.15(d, 1H, J=8.6Hz), 6.56(d, 1H, J=8.6Hz), 6.69(dd, 1H, J=2.8, 8.6Hz), 6.84(d, 1H, J=2.8Hz): |
| $^{13}$CNMR(CDCl$_3$)δ = | 25.2, 40.3, 52.4, 55.7, 55.8, 66.6, 75.8, 113.6, 115.9, 116.2, 123.1, 137.3, 153.2, 171.8; (minor): |
| $^{13}$HNMR(CDCl$_3$)δ = | 2.10–2.33(m, 2H), 2.60–2.69(m, 1H), 3.58(d, 1H, J=9.5Hz), 3.74(s, 3H), 3.77–3.85(m, 4H), 3.92–4.00(m, 1H), 4.62(d, 1H, J=6.3Hz), 6.63 (d, 1H, J=8.8Hz), 6.73(dd, 1H, J=2.9, 8.8Hz), 6.89(d, 1H, J=2.9Hz): |
| $^{13}$CNMR(CDCl$_3$)δ = | 29.6, 39.3, 52.4, 55.7, 56.2, 65.8, 75.1, 113.9, 116.5, 116.6, 121.4, 136.9, 153.0, 172.8: IR(neat) 1622, 1737, 3367cm$^{-1}$. |

Further, the same reaction was conducted using Compounds (5a)–(5c) as the starting material and Compounds (9a)–(9d) as the alkene. The resulting products, as well as their yield and selectivity are shown in the following table.

TABLE 14

| Materials | Tetrahydroquinoline Derivatives | | Yield | Selectivity |
|---|---|---|---|---|
| 5a + 9a | [structure: tetrahydroquinoline fused with furan, 8-OMe, 4-CO₂Me] | (10a) | 72%[a] | 68/32 |
| 5b + 9a | [structure: tetrahydroquinoline fused with furan, 8-Cl, 4-CO₂Me] | (10b) | 84%[a] | 60/32 |
| 5b + 9b | [structure: 4-Me, 4-Ph, 6-Cl, 2-CO₂Me tetrahydroquinoline] | (10c) | 78%[a] | 75/25 |
| 5c + 9b | [structure: 4-Me, 4-Ph, 6-Br, 2-CO₂Me tetrahydroquinoline] | (10d) | quant[a] | 68/32 |
| 5b + 9c | [structure: indene-fused tetrahydroquinoline, Cl, CO₂Me] | (10e) | 95%[a] | 95/5 |
| 5c + 9d | [structure: indane-fused tetrahydroquinoline with Me, Br, CO₂Me] | (10f) | quant[a] | 93/7 |

[a]Based on 5d

The identification results for Compounds (10b)–(10f) are shown in the following Tables 15–19,

TABLE 15

| Compound (10b) | |
|---|---|
| (major): $^1$HNMR(CDCl$_3$)δ = | 1.97–2.29(m, 2H), 2.53–2.60(m, 1H), 3.57(d, 1H, J=9.0Hz), 3.70–3.83(m, 4H), 3.89(dd, 1H, J=5.4, 8.4Hz), 4.53(d, 1H, J=6.1Hz), 6.54(d, 1H, J=8.7Hz), 6.99(dd, 1H, J=2.4, 8.7Hz), 7.23(d, 1H, J=2.4Hz): |
| $^{13}$CNMR(CDCl$_3$)δ = | 29.4, 38.8, 52.6, 55.3, 65.6, 116.2, 121.7, 123.5, 128.9, 130.1, 141.6, 172.5: |
| (minor): $^1$HNMR(CDCl$_3$)δ = | 1.70–2.00(m, 2H), 2.95–3.10(m, 1H), 3.65–3.80(m, 5H), 4.14(d, 1H, J=3.1Hz), 5.07(d, 1H, J=7.9Hz), 6.47(d, 1H, J=8.6 HZ), 6.95(dd, 1H, J=2.3, 8.6Hz), 7.20(d, 1H, J=2.3Hz): |
| $^{13}$CNMR(CDCl$_3$)δ = | 25.0, 39.9, 52.6, 54.9, 66.6, 115.9, 123.4, 123.8, 128.6, 129.5, 141.7, 172,5: IR (neat)1649, 1739cm$^{-1}$: MS(EI)m/z=267. |

TABLE 16

| Compound (10c) | |
|---|---|
| (major): $^1$HNMR(CDCl$_3$)δ = | 1.64(s, 3H), 2.15(dd, 1HJ=4.1, 13.4Hz), 2.24(dd, 1H, J=10.1, 13.4Hz), 3.53(s, 3H), 4.10(dd, 1H, J=4.1, 10.1Hz), 6.53(d, 1H, J=8.5Hz), 6.60(d, 1H, J=2.4Hz), 6.90 (dd, 1H, J=2.4, 8.5Hz), 7.11–7.25(m, 5H): |
| $^{13}$CNMR(CDCl$_3$)δ = | 28.7, 41.20, 41.23, 51.4, 52.3, 115.9, 122.2, 126.4, 127.2, 127.3, 128.1, 128.6, 130.3, 141.2, 148.0, 173.2: |
| (minor): $^1$HNMR(CDCl$_3$)δ = | 1.67(s, 3H), 1.87(dd, 1HJ=12.3, 12.9Hz), 2.43(dd, 1H, J=3.5, 12.9Hz), 3.52(dd, 1H, J=3.5, (2.3Hz), 3.66(s, 3H), 6.33(d, 1H, J=9.0Hz), 6.95–7.32(m, 5H): |
| $^{13}$CNMR(CDCl$_3$)δ = | 29.0, 40.1, 41.1, 50.8, 52.4, 114.6, 115.6, 126.3, 126.9, 127.4, 127.6, 128.4, 129.1, 141.5, 147.9, 173.4: IR(neat)1713, 3384cm$^{-1}$: MS(EI)m/z=315. |

TABLE 17

| Compound (10d) | |
|---|---|
| (major): $^1$HNMR(CDCl$_3$)δ = | 1.71(s, 3H), 2.21(dd, 1HJ=4.1, 13.3Hz), 2.30(dd, 1H, J=10.1, 13.3Hz), 3.59(s, 3H), 4.16(dd, 1H, J=4.1, 10.1Hz), 6.54(d, 1H, J=8.6Hz), 6.80(d, 1H, J=2.1Hz), 7.10 (dd, 1H, J=2.1, 8.6Hz), 7.15–7.40(m, 5H): |
| $^{13}$CNMR(CDCl$_3$)δ = | 28.7, 41.2, 51.4, 52.3, 100.5, 109.3, 116.3, 126.4, 127.3, 128.2, 128.9, 130.0, 130.7, 131.45, 131.51, 132.2, 141.6, 147.9, 173.1: |
| (minor): $^1$HNMR(CDCl$_3$)δ = | 1.75(s, 3H), 1.94(dd, 1HJ=12.2, 12.8Hz), 2.50(dd, 1H, J=3.4, 12.8Hz), 3.59(dd, 1H, J=3.4, 12.8Hz), 3.73(s, 3H), 6.55(d, 1H, J=8.6Hz), 7.06(d, 2H, J=7.2Hz), 7.18(dd, 1H, J=2.0, 6.4Hz), 7.30–7.43(m, 3H): |
| $^{13}$CNMR(CDCl$_3$)δ = | 29.0, 40.1, 41.1, 50.8, 52.4, 109.1, 116.0, 126.3, 126.9, 128.2, 128.4, 130.2, 130.5, 141.9, 147.9, 173.4: IR(neat)1713, 3408cm$^{-1}$: MS(EI)m/z=359. |

TABLE 18

| Compound (10e) | |
|---|---|
| $^1$HNMR(CDCl$_3$)δ = | 2.68(dd, 1H, J=8.0, 15.4Hz), 3.02(dd, 1H, J=10.2, 15.4Hz), 3.29–3.39(m, 1H), 3.71(s, 3H), 4.10,(d, 1H, J=3.2Hz), 4.33(d, 1H, J=8.3Hz), |

TABLE 18-continued

| Compound (10e) | |
|---|---|
| | 6.42(d, 1H, J=8.6Hz), 6.80(dd, 1H, J=2.2, 8.6Hz), 7.00–7.15(m, 3H): |
| $^{13}$CNMR(CDCl$_3$)δ = | 31.6, 42.3, 45.5, 52.3, 116.5, 123.2, 124.8, 124.9, 125.1, 126.7, 126.8, 127.3, 128.7, 141.8, 142.1, 144.9, 171.9: IR(neat)1713, 3409cm$^{-1}$: MS(EI)m/z=313. |

TABLE 19

| Compound (10f) | |
|---|---|
| $^1$HNMR(CDCl$_3$)δ = | 1.75(s, 3H), 2.58–2.70(m, 1H), 2.90–3.02(m, 2H), 3.85(s, 3H), 4.31(d, 1H, J=2.4Hz)6.45(d, 1H, J=8.8Hz), 6.99(dd, 1H, J=2.4, 8.8Hz), 7.080–7.30(m, 4H), 7.48(d, 1H, J=7.2Hz): |
| $^{13}$CNMR(CDCl$_3$)δ = | 29.6, 30.6, 48.1, 49.7, 52.1, 52.5, 110.0, 116.6, 123.4, 124.8, 126.8, 127.2, 128.8, 129.7, 131.5, 140.7, 141.0, 148.7, 172.4: IR(neat)1712, 3409cm$^{-1}$: MS(EI)m/z=371. |

In each of the reactions, the solid phase reaction proceeded smoothly and tetrahydroquinoline derivatives corresponding to each starting material and reactant were obtained at high yield. Further, it was shown that even halogenated compounds were stable in these reactions.

INDUSTRIAL APPLICABILITY

As has been described above in detail, a new polymer-immobilized α-iminoester has been provided by the invention of the present application. Using this polymer-immobilized α-iminoester, α-aminoester derivatives, which are known to be important in the field of biochemistry, can be synthesized in high yield.

What is claimed is:

1. A polymer-immobilized α-iminoester, which is represented by the following formula (1):

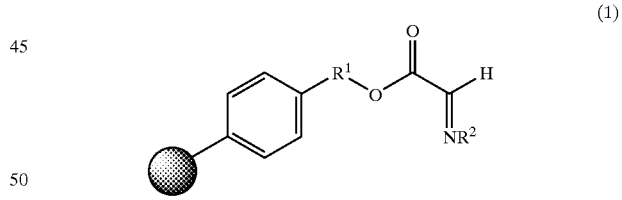

(1)

wherein R$^1$ represents an alkyl chain of 1 or more carbon atom(s), and R$^2$ represents a hydrogen atom, halogen atom, alkyl group, alkylene group, p-substituted phenyl group or alkoxy group, wherein

wherein the polymer is a copoly (styrene-divinyl benzene) resin.

2. A method of producing an α-aminoester, which comprises reacting the polymer-immobilized α-iminoester of the following formula (1):

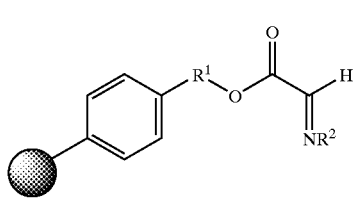
(1)

wherein $R^1$ represents an alkyl chain of 1 or more carbon atom(s), and $R^2$ represents a hydrogen atom, halogen atom, alkyl group, alkylene group, p-substituted phenyl group or alkoxy group,
wherein

 = a polymer, and wherein the polymer is a copoly (styrene-divinyl benzene) resin,
with a nucleophile.

3. The polymer-immobilized α-iminoester of claim 1 wherein $R^1$ is an alkyl chain of 1 to 3 carbon atoms.

4. The polymer-immobilized α-iminoester of claim 1 wherein $R^2$ is p-halogenated phenyl or p-methoxyphenyl.

5. A method of producing a tetrahydroquinoline, which comprises reacting the polymer-immobilized α-iminoester of the following formula (1):

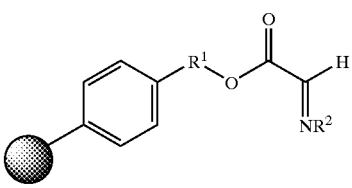
(1)

wherein $R^1$ represents an alkyl chain of 1 or more carbon atom(s), and $R^2$ represents a hydrogen atom, halogen atom, alkyl group, alkylene group, p-substituted phenyl group or alkoxy group,
wherein

 = a polymer, and wherein the polymer is a copoly (styrene-divinyl benzene) resin,
with an alkene.

* * * * *